United States Patent
Aoki et al.

(10) Patent No.: US 7,468,189 B2
(45) Date of Patent: *Dec. 23, 2008

(54) NEUROPATHIC PAIN TREATMENT METHOD

(75) Inventors: Roger Kei Aoki, Coto De Caza, CA (US); Minglei Cui, Irvine, CA (US); Stephen W. Jenkins, Mission Viejo, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/942,985

(22) Filed: Nov. 20, 2007

(65) Prior Publication Data

US 2008/0138364 A1 Jun. 12, 2008

Related U.S. Application Data

(63) Continuation of application No. 11/205,380, filed on Aug. 16, 2005, now Pat. No. 7,294,339, which is a continuation of application No. 10/630,206, filed on Jul. 29, 2003, now Pat. No. 7,361,358, which is a continuation of application No. 10/199,222, filed on Jul. 18, 2002, now Pat. No. 6,869,610, which is a continuation of application No. 09/550,371, filed on Apr. 14, 2000, now Pat. No. 6,464,986.

(51) Int. Cl.
*A61K 39/08* (2006.01)
*A61K 39/02* (2006.01)

(52) U.S. Cl. .................. 424/239.1; 424/236.1; 424/9.1; 514/2; 514/12; 530/350; 435/252.7

(58) Field of Classification Search ............ 424/239.1, 424/236.1, 9.1; 514/2, 12; 530/350; 435/252.7
See application file for complete search history.

(56) References Cited

U.S. PATENT DOCUMENTS

| | | | |
|---|---|---|---|
| 5,714,468 A | 2/1998 | Binder | |
| 5,766,605 A | 6/1998 | Sanders et al. | |
| 5,989,545 A | 11/1999 | Foster et al. | |
| 6,063,768 A * | 5/2000 | First ............................ | 514/14 |
| 6,113,915 A | 9/2000 | Aoki | |
| 6,464,986 B1 | 10/2002 | Aoiki et al. | |
| 6,869,610 B2 * | 3/2005 | Aoki et al. ................ | 424/239.1 |
| 7,067,137 B2 * | 6/2006 | Aoki et al. ................ | 424/239.1 |
| 7,172,763 B2 | 2/2007 | Aoiki et al. | |
| 7,211,262 B2 | 5/2007 | Aoiki et al. | |
| 7,276,245 B2 * | 10/2007 | Aoki et al. ................ | 424/239.1 |
| 7,288,260 B2 | 10/2007 | Aoiki et al. | |
| 7,291,344 B2 | 11/2007 | Aoiki et al. | |
| 7,294,339 B2 * | 11/2007 | Aoki et al. ................ | 424/239.1 |
| 7,361,358 B2 * | 4/2008 | Aoki et al. ................ | 424/239.1 |
| 2006/0039916 A1 * | 2/2006 | Aoki et al. ................ | 424/184.1 |

FOREIGN PATENT DOCUMENTS

| | | |
|---|---|---|
| WO | WO94/15629 | 7/1994 |
| WO | WO 95/30431 | 11/1995 |
| WO | WO96/33273 | 10/1996 |
| WO | WO 97/34624 | 9/1997 |
| WO | WO98/07864 | 2/1998 |
| WO | WO99/17806 | 4/1999 |

OTHER PUBLICATIONS

Barwood, Shane, et al.; Analgesic Effects of Botulinum Toxin A: A Randomized, Placebo-Controlled Clinical Trial; *Developmental Medicine & Child Neurology*, 2000; 42:116-121.

Bigalke, H., et al.; Botulinum A Neurotoxin Inhibits Non-Cholinergic Synaptic Transmission in Mouse Spinal Cord Neurons in Culture; *Brain Research*, 360 (1985); 318-324.

Bigalke, H., et al.; Tetanus Toxin and Botulinum A. Toxin Inhibit Release and Uptake of Various Transmitters, as Studied with Particulate Preparations from Rat Brain and Spinal Cord; *Naunyn-Schmiedeberg's Arch. Pharmacol* (1981); 316:244-251.

Cheshire, et al.; Botulinum Toxin in the Treatment of Myofascial Pain Syndrome; *Pain*, 1994; 59(1):65-9.

DiStefano, P. S., et al.; Receptor Mediated Retrograde Axonal Transport of Neurotrophic Factors is Increased After Peripheral Nerve Injury; *Progress in Brain Research* (1994); vol. 103; Chapter 4; 35-42.

Dixon, Wl J.; Efficient Analysis of Experimental Observations; *Ann. Rev. Pharmacol. Toxicol.* (1980); 20:441-462.

Dubuisson, D., et al.; The Formalin Test: A Quantitative Study of the Analgesic Effects of Morphine, Meperidine, and Brain Stem Stimulation in Rats and Cats; *Pain* (1977); 4:161-174.

Duc, C., et al., Ultrastructural Localization of SNAP-25 Within the Rat Spinal Cord and Peripheral Nervous System; *The Journal of Comparative Neurology* (1995); 356:152-163.

(Continued)

*Primary Examiner*—Chih-Min Kam
(74) *Attorney, Agent, or Firm*—Claude L. Nassif; Stephen Donovan; Martin Voet

(57) ABSTRACT

Methods for treating a non-spasm caused pain by peripheral administration to a patient of a therapeutically effective amount of a neurotoxin, such as a botulinum toxin.

9 Claims, 2 Drawing Sheets

OTHER PUBLICATIONS

Figure 1:
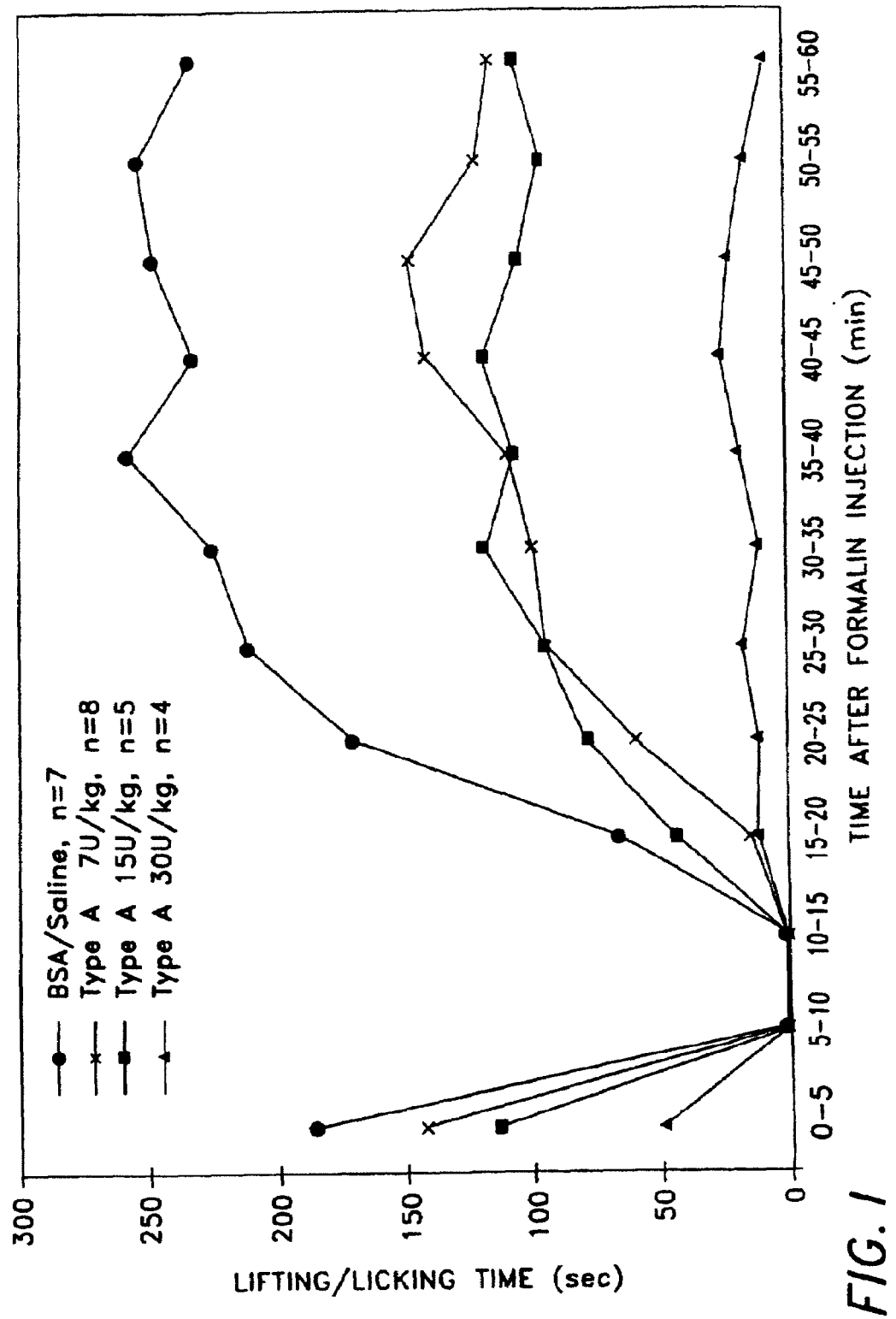

Fauci, A.S., et al. (Editors); Harrison's Principles of Internal Medicine, 14th Edition (1998); McGraw-Hill; 2064-2065.

Garner, C.G., et al.; Time Course of Distant Effects of Local Injections of Botulinum Toxin; *Movement Disorders*; vol. 8, No. 1; 1993.

Habermann, E.; Inhibition by Tetanus and Botulinum A Toxin of the Release of ($^3$H) noradrenaline and ($^3$H) GABA from Rat Brain Homogenate; *Experientia* 44 (1988); 224-226.

Habermann, E.; I-Labeled Neurotoxin from Clostridium Botulinum A: Preparation, Binding to Synaptosomes and Ascent to the Spinal Cord; *Naunyn Schmiedeberg's Arch. Pharmacol.*; 281, 47-56 (1974).

Habermann, E., et al.; Tetanus Toxin and Botulinum A and C Neurotoxins Inhibit Noradrenaline Release from Cultured Mouse Brain; *Journal of Neurochemistry*; vol. 51; No. 2 (1988); 522-527.

Hagenah, R., et al.; Efffects of Type A Botulinum Toxin on the Cholinergic Transmission at Spinal Renshaw Cells and on the Inhibitory Action at Ia Inhibitory Interneurones; *Naunyn-Schmiedeberg's Arch. Pharmacol.*; 299, 267-272 (1977).

Halpern, J.L., et al.; *Neurospecific Binding, Internalization, and Retrograde Axonal Transport*; pp. 221-241. in Curr. Top. Microbiol. Immunol. 1995.

Johnson, E., et al.; Biomedical Aspects of Botulinum Toxin; *J. Toxicol.-Toxin Reviews*; Feb. 18, 1999; 18(1):1-15.

Jung, H. H., et al.; Expression of Neurotransmitter Genes in Rat Spinal Motoneurons After Chemodenervation with Botulinum Toxin; *Neuroscience* (1997); vol. 78, No. 2; 469-479.

Kim, S. H., et al.; An Experimental Model for Peripheral Neuropathy Produced by Segmental Spinal Nerve Ligation in the Rat; *Pain*, 50 (1992); 355-363.

Li et al.; *Biochemistry*; 33:7014-7020 (1994).

Mochida, S., et al.; Impairment of Syntaxin by Botulinum Neurotoxin $C_1$ or Antibodies Inhibits Acetylcholine Release but not $Ca^{2+}$Channel Activity; *Neuroscience* (1995); vol. 65; No. 3; 905-915.

Naumann, et al.; Botulinum Toxin Type A in the Treatment of Focal, Axillary and Palmar Hyperhidrosis and Other Hyperhidrotic Conditions; *European Journal of Neurology*, 1999; vol. 6(supp14):S3-S10 and S111-S115.

Nelson, P.G., et al.; Mouse Spinal Cord in Cell Culture. IV. Modulation of Inhibitory Synaptic Function; *Journal of Neurophysiology*; vol. 40, No. 5; Sep. 1977; 1178-1187.

Osen-Sand, A., et al.; Inhibition of Axonal Growth by SNAP-25 Antisense Oligonucleotides in vitro and in vivo; *Nature*; Jul. 29, 1993; vol. 364; 445-448.

Pearce, L. B., et al.; Pharmacologic Characterization of Botulinum Toxin for Basic Science and Medicine; *Toxicon* (1997); vol. 35, No. 9; 1373-1412.

Ragona, et al.; Management of Parotid Sialocele with Botulinum Toxin; *Laryngoscope*, 109:Aug. 1999; p. 1344-36..

Ransom, B.R., et al.; Mouse Spinal Cord in Cell Culture. I. Morphology and Intrinsic Neuronal Electrophysiologic Properties; *Journal of Neurophysiology*; vol. 40, No. 5; Sep. 1977; 1132-1150.

Ransom, B.R., et al.; Mouse Spinal Cord in Cell Culture. II. Synaptic Activity and Circuit Behavior; *Journal of Neurophysiology*; vol. 40, No. 5; Sep. 1977; 1151-1162.

Ransom, B.R., et al.; Mouse Spinal Cord in Cell Culture. III. Neuronal Chemosensitivity and its Relationship to Synaptic Activity; *Journal of Neurophysiology*; vol. 40, No. 5; Sep. 1977; 1163-1177.

Rees, H., et al.; Do Dorsal Root Reflexes Augment Peripheral Inflammation?; *Neuro Report*; vol. 5, No. 7; Mar. 21, 1994; 821-824.

Sanchez-Prieto, J., et al.; Botulinum Toxin A Blocks Glutamate Exocytosis from Guinea-Pig Cerebral Cortical Synaptosomes; *Eur. J. Biochem.* (1987); 165:675-681.

Shantz, E.J., et al.; Properties and Use of Botulinum Toxin and Other Microbial Neurotoxins in Medicine; *Microbiol Rev.*; 56:80-99 (1992).

Simpson, L.; Botulinum Toxin: Potent Poison, Potent Medicine; *Hospital Practice*; Apr. 15, 1999; 34(4):87-91.

Singh, B.R.; Critical Aspects of Bacterial Protein Toxins; *Natural Toxins II* (1996); Plenum Press, New York; pp. 63-84.

Tonra, J. R., et al.; Axotomy Upregulates the Anterograde Transport and Expression of Brain-Derived Neurotrophic Factor by Sensory Neurons; *The Journal of Neuroscience*; Jun. 1, 1998; 18(11):4374-4383.

Tsuda, M., et al.; In vivo Pathway of Thermal Hyperalgesia by Intrathecal Administration of a $\alpha$, $\beta$-methylene ATP in Mouse Spinal Cord: Involvement of the Glutamate-NMDA Receptor System; *Br. J. Pharmacol* (1999); 127(2):449-456.

Wiegand, H., et al.; The Action of Botulinum A Neurotoxin on the Inhibition by Antidromic Stimulation of the Lumbar Monosynaptic Reflex; *Naunyn-Schmiedeberg's Arch. Pharmacol.* (1977); 298:235-238.

Wiegand, H., et al.; I-Labelled Botulinum A Neurotoxin: Pharmacokinetics in Cats After Intramuscular Injection; *Nauyn-Schmiedeberg's Arch. Pharmacol.*; 292, 161-165 (1976).

Williamson, L. C., et al.; Clostridial Neurotoxins and Substrate Proteolysis in Intact Neurons; *The Journal of Biological Chemistry*; Mar. 29, 1996; vol. 271:13; 7694-7699.

Williamson, L. C., et al.; Differential Effects of Tetanus Toxin on Inhibitory and Excitatory Neurotransmitter Release from Mammalian Spinal Cord Cells in Culture; *Journal of Neurochemistry*; 1992; vol. 59:6; 2148-2157.

Willis, W. D.; Pain; *The Rat Nervous System*; Second Edition; 1995; Academic Press, Inc.; pp. 725-750.

Woolf, C. J., et al.; Neuropathic Pain: Aetiology, Symptoms, Mechanisms, and Management; *The Lancet*; Jun. 5, 1999; vol. 353; 1959-1964.

Yaksh, T. L., et al.; Chronic Catheterization of the Spinal Subarachnoid Space; *Physiology & Behavior* (1976); vol. 17:1031-1036.

Zhou et al., *Biochemistry*; 34:15175-15181 (1995).

Guyer, B., *Mechanism of botulinum toxin in the relief of chronic pain*, Current Review of Pain, 1999, 3:427-431, XP-001031379.

Carruthers, A., et al., *Improvement of tension-type headache when treating wrinkles with botulinum toxin A injections*, Headache, Oct. 1999:39:662-665, XP-001031356.

Diaz, J., et al., *Management of post-thoracotomy pseudoangina and myofascial pain with botulinum toxin*, Anesthesiology, V 91, No. 3, Sep. 1999, pp. 877-879, XP-001031347.

Silberstein, S., et al., *Botulinum toxin type A as a migraine preventive treatment*, Headache 2000:40:445-450, XP-002182692.

Gobel, H., et al., *Evidence-based medicine: botulinum toxin A in migraine and tension-type headache*, Journal of Neurology, 2001 248 Supp 1: I/34-I/38, XP-002182693.

U.S. Appl. No. 11/205,357, filed Aug. 16, 2005, Aoiki et al.

* cited by examiner

NEUROPATHIC PAIN TREATMENT METHOD

CROSS REFERENCE

This application is a continuation of U.S. application Ser. No. 11/205,380, filed Aug. 16, 2005, now U.S. Pat. No. 7,294,339, which is a continuation of U.S. application Ser. No. 10/630,206, filed Jul. 29, 2003, now U.S. Pat. No. 7,361,358, which is a continuation of U.S. application Ser. No. 10/199,222, filed Jul. 18, 2002, now U.S. Pat. No. 6,869,610, which is a continuation of U.S. Ser. No. 09/550,371, filed Apr. 14, 2000, now U.S. Pat. No. 6,464,986 B1, the entire contents of which prior applications and patents are incorporated herein by reference in their entireties.

BACKGROUND

The present invention relates to methods for treating pain. In particular, the present invention relates to methods for treating pain by peripheral administration of a neurotoxin.

Many, if not most ailments of the body cause pain. Generally pain is experienced when the free nerve endings which constitute the pain receptors in the skin as well as in certain internal tissues are subjected to mechanical, thermal, chemical or other noxious stimuli. The pain receptors can transmit signals along afferent neurons into the central nervous system and thence to the brain.

The causes of pain can include inflammation, injury, disease, muscle spasm and the onset of a neuropathic event or syndrome. Ineffectively treated pain can be devastating to the person experiencing it by limiting function, reducing mobility, complicating sleep, and dramatically interfering with the quality of life.

A muscle spasm can lead to stimulation of mechanosensitive pain receptors thereby causing a sensation of pain. Thus, pain can arise from or be due to a muscle spasm. Additionally, the spasm can indirectly stimulate the pain receptors by compressing onto blood vessels, causing ischemia in the tissue, which in turn releases pain inducing substances that stimulate pain receptors to cause pain sensations. Furthermore, a muscle spasm can cause a localized pH reduction which can be perceived as or which can engender pain signals. Hence, pain can be a secondary effect of a muscle spasm or muscle hypertonicity.

Inflammatory pain can occur when tissue is damaged, as can result from surgery or due to an adverse physical, chemical or thermal event or to infection by a biologic agent. When a tissue is damaged, a host of endogenous pain inducing substances, for example bradykinin and histamine can be released from the injured tissue. The pain inducing substances can bind to receptors on the sensory nerve terminals and thereby initiate afferent pain signals.

Additionally, pain inducing substances can be released from nociceptive afferent terminals, and neuropeptides released from sensory terminals can accentuate an inflammatory response. Thus, during inflammation there can be a sprouting of peptidergic peripheral fibers and an increased content of peptide, with many fibers showing a coexistence of substance P (SP) and calcitonin gene related peptide (CGRP). Substance P can induce contraction of endothelia cells, which in turn causes plasma extravasation to allow other substances (bradykinin, ATP, histamine) to gain access to the cite of injury and the afferent nerve terminals. Substance P release by the sensory nerve terminal can also degranulate mast cell. This process has been considered to be an important factor in neurogenic inflammation due to the release of inflammatory mediators such as histamine and serotonin and the release of proteolytic enzymes which catalyze the production of bradykinin. CGRP apparently does not produce plasma extravasation but is a powerful vasodilator and also act synergistically with SP and other inflammatory mediators to enhance plasma extravasation. All the above listed inflammatory mediators can either sensitize nociceptors or produce pain.

After activation of the primary sensory afferent neurons the next step in the transduction of sensory signals can be activation of projection neurons, which carry the signal, via the spinothalamic tract, to higher parts of the central nervous system such as the thalamic nuclei. The cell bodies of these neurons (other than those related to the cranial nerves) are located in the dorsal horn of the spinal cord. Here also one can find the synapses between the primary afferents and the projection neurons. The dorsal horn is organized into a series of laminae that are stacked, with lamina I being most dorsal followed by lamina II, etc. The different classes of primary afferents make synapses in different laminae. For cutaneous primary afferents, C-fibers make synapses in laminae I and II, A delta-fibers in laminae I, II, and V, and A beta-fibers in laminae III, IV, and V. Deeper laminae (V-VII, X) are thought to be involved in the sensory pathways arriving from deeper tissues such as muscles and the viscera.

The predominant neurotransmitters at the synapses between primary afferent neurons and projection neurons are substance P, glutamate, CGRP and neuropeptide Y. The efficiency of transmission of these synapses can be altered via descending pathways and by local interneurons in the spinal cord. These modulatory neurons can release a number of mediators that are either inhibitory (e.g. opioid peptides, glycine) or excitatory (e.g. nitric oxide, cholecystokinin), to provide a mechanism for enhancing or reducing awareness of sensations.

Although inflammatory pain is generally reversible and subsides when the injured tissue has been repaired or the pain inducing stimulus removed, present methods for treating inflammatory pain have many drawbacks and deficiencies. Thus, the typical oral, parenteral or topical administration of an analgesic drug to treat the symptoms of pain or of, for example, an antibiotic to treat inflammatory pain causation factors can result in widespread systemic distribution of the drug and undesirable side effects. Additionally, current therapy for inflammatory pain suffers from short drug efficacy durations which necessitate frequent drug re-administration with possible resulting drug resistance, antibody development and/or drug dependence and addiction, all of which are unsatisfactory. Furthermore, frequent drug administration increases the expense of the regimen to the patient and can require the patient to remember to adhere to a dosing schedule.

Examples of treatments for inflammation and muscle pain include non-steroidal anti-inflammatory drugs (NSAIDS), including aspirin and ibuprofen; and opioids, such as morphine.

NSAIDs alleviate pain by inhibiting the production of prostaglandins released by damaged tissues. Prostaglandins have been shown to be peripheral mediators of pain and inflammation, as in arthritic diseases, and a reduction in their concentration provides relief to patients. It has been suggested that prostaglandins are involved in the mediation of pain in the spinal cord and the brain, which may explain the analgesic effects of NSAIDS in some pain states that do not involve inflammation or peripheral tissue damage. However, prostaglandins are only one of several mediators of pain. As such, NSAIDs have a ceiling of activity above which increasing doses do not give more pain relief. Furthermore, they have side effects that limit their usefulness. For example, NSAIDs can cause irritation of the gastrointestinal tract and prolonged use may lead to the development of extensive ulceration of the gut. This is particularly true in elderly patients who frequently use NSAIDs for their arthritis conditions.

The therapeutic actions of opioids are in the spinal cord. Opioids inhibit the efficiency of neurotransmission between the primary sensory afferents (principally C-fibers) and the projection neurons. They achieve this by causing a prolonged hyperpolarization of both elements of these synapses. The use of opioids is effective in alleviating most types of acute pain and chronic malignant pain. There are, however, a number of chronic malignant pain conditions which are partly or completely refractory to opioid analgesia, particularly those which involve nerve compression, e.g. by tumor formation. Unfortunately opioids also have unwanted side-effects including: (1) depression of the respiratory system, (2) constipation, and (3) psychoactive effects including sedation and euphoria. These side effects occur at doses similar to those that produce analgesia and therefore limit the doses that can be given to patients. Additionally, opioids such as morphine and heroin are well-known drugs of abuse that lead to physical dependence, which also involves the development of tolerance. With the development of tolerance, the dose of a drug required to produce the same analgesic effect increases with time. This may lead to a condition in which the doses required to alleviate the pain are life-threatening due to previously mentioned side-effects.

Although pain arising from inflammation and muscle spasm can be initiated by mechanical or chemical stimulation of the primary sensory neuron free terminal, neuropathic pain does not require an initial stimulus to the peripheral, free nerve terminal. Neuropathic pain is a persistent or chronic pain syndrome that can result from damage to the nervous system, the peripheral nerves, the dorsal root ganglion, dorsal root, or to the central nervous system.

Neuropathic pain syndromes include allodynia, various neuralgias such as post herpetic neuralgia and trigeminal neuralgia, phantom pain, and complex regional pain syndromes, such as reflex sympathetic dystrophy and causalgia. Causalgia is often characterized by spontaneous burning pain combined with hyperalgesia and allodynia.

Tragically there is no existing method for adequately, predictably and specifically treating established neuropathic pain (Woolf C. et al., *Neuropathic Pain: Aetiology, Symptoms, Mechanisms, and Management,* Lancet 1999; 353: 1959-64) as present treatment methods for neuropathic pain consists of merely trying to help the patient cope through psychological or occupational therapy, rather than by reducing or eliminating the pain experienced.

For example, current methods to treat neuropathic pain include administration of local anesthetic blocks targeted to trigger points, peripheral nerves, plexi, dorsal roots, and to the sympathetic nervous system. However, these treatments have only short-lived antinociceptive effects. Additionally, longer lasting analgesic treatment methods, such as blocks by phenol injection or cryotherapy raise a considerable risk of irreversible functional impairment. Furthermore, chronic epidural or intrathecal (collectively "intraspinal") administration of drugs such as clonidine, steroids, opioids or midazolam have significant side effects and questionable efficacy.

Botulinum Toxin

The anaerobic, gram positive bacterium *Clostridium botulinum* produces a potent polypeptide neurotoxin, botulinum toxin, which causes a neuroparalytic illness in humans and animals referred to as botulism. The spores of *Clostridium botulinum* are found in soil and can grow in improperly sterilized and sealed food containers of home based canneries, which are the cause of many of the cases of botulism. The effects of botulism typically appear 18 to 36 hours after eating the foodstuffs infected with a *Clostridium botulinum* culture or spores. The botulinum toxin can apparently pass unattenuated through the lining of the gut and attack peripheral motor neurons. Symptoms of botulinum toxin intoxication can progress from difficulty walking, swallowing, and speaking to paralysis of the respiratory muscles and death.

Botulinum toxin type A is the most lethal natural biological agent known to man. About 50 picograms of a commercially available botulinum toxin type A (purified neurotoxin complex)[1] is a $LD_{50}$ in mice (i.e. 1 unit). One unit of BOTOX® contains about 50 picograms of botulinum toxin type A complex. Interestingly, on a molar basis, botulinum toxin type A is about 1.8 billion times more lethal than diphtheria, about 600 million times more lethal than sodium cyanide, about 30 million times more lethal than cobra toxin and about 12 million times more lethal than cholera. Singh, *Critical Aspects of Bacterial Protein Toxins,* pages 63-84 (chapter 4) of Natural Toxins II, edited by B. R. Singh et al., Plenum Press, New York (1976) (where the stated $LD_{50}$ of botulinum toxin type A of 0.3 ng equals 1 U is corrected for the fact that about 0.05 ng of BOTOX® equals 1 unit). One unit (U) of botulinum toxin is defined as the $LD_{50}$ upon intraperitoneal injection into female Swiss Webster mice weighing 18 to 20 grams each.

[1] Available from Allergan, Inc., of Irvine, Calif. under the tradename BOTOX® in 100 unit vials)

Seven immunologically distinct botulinum neurotoxins have been characterized, these being respectively botulinum neurotoxin serotypes A, B, $C_1$, D, E, F and G each of which is distinguished by neutralization with type-specific antibodies. The different serotypes of botulinum toxin vary in the animal species that they affect and in the severity and duration of the paralysis they evoke. For example, it has been determined that botulinum toxin type A is 500 times more potent, as measured by the rate of paralysis produced in the rat, than is botulinum toxin type B. Additionally, botulinum toxin type B has been determined to be non-toxic in primates at a dose of 480 U/kg which is about 12 times the primate $LD_{50}$ for botulinum toxin type A. Botulinum toxin apparently binds with high affinity to cholinergic motor neurons, is translocated into the neuron and blocks the release of acetylcholine.

Regardless of serotype, the molecular mechanism of toxin intoxication appears to be similar and to involve at least three steps or stages. In the first step of the process, the toxin binds to the presynaptic membrane of the target neuron through a specific interaction between the heavy chain, H chain, and a cell surface receptor; the receptor is thought to be different for each type of botulinum toxin and for tetanus toxin. The carboxyl end segment of the H chain, $H_C$, appears to be important for targeting of the toxin to the cell surface.

In the second step, the toxin crosses the plasma membrane of the poisoned cell. The toxin is first engulfed by the cell through receptor-mediated endocytosis, and an endosome containing the toxin is formed. The toxin then escapes the endosome into the cytoplasm of the cell. This step is thought to be mediated by the amino end segment of the H chain, $H_N$, which triggers a conformational change of the toxin in response to a pH of about 5.5 or lower. Endosomes are known to possess a proton pump which decreases intra-endosomal pH. The conformational shift exposes hydrophobic residues in the toxin, which permits the toxin to embed itself in the endosomal membrane. The toxin (or at a minimum the light chain) then translocates through the endosomal membrane into the cytoplasm.

The last step of the mechanism of botulinum toxin activity appears to involve reduction of the disulfide bond joining the heavy chain, H chain, and the light chain, L chain. The entire toxic activity of botulinum and tetanus toxins is contained in the L chain of the holotoxin; the L chain is a zinc ($Zn^{++}$) endopeptidase which selectively cleaves proteins essential for recognition and docking of neurotransmitter-containing vesicles with the cytoplasmic surface of the plasma membrane, and fusion of the vesicles with the plasma membrane. Tetanus neurotoxin, botulinum toxin/B/D/F, and/G cause degradation of synaptobrevin (also called vesicle-associated membrane protein (VAMP)), a synaptosomal membrane protein. Most of the VAMP present at the cytoplasmic surface of the synaptic vesicle is removed as a result of any one of these cleavage events. Serotype A and E cleave SNAP-25. Serotype $C_1$ was originally thought to cleave syntaxin, but was found to cleave syntaxin and SNAP-25. Each toxin specifically cleaves a different bond (except tetanus and type B which cleave the same bond).

Botulinum toxins have been used in clinical settings for the treatment of neuromuscular disorders characterized by hyperactive skeletal muscles. Botulinum toxin type A has been approved by the U.S. Food and Drug Administration for the treatment of blepharospasm, strabismus and hemifacial spasm. Non-type A botulinum toxin serotypes apparently have a lower potency and/or a shorter duration of activity as compared to botulinum toxin type A. Clinical effects of peripheral intramuscular botulinum toxin type A are usually seen within one week of injection. The typical duration of symptomatic relief from a single intramuscular injection of botulinum toxin type A averages about three months.

Although all the botulinum toxins serotypes apparently inhibit release of the neurotransmitter acetylcholine at the neuromuscular junction, they do so by affecting different neurosecretory proteins and/or cleaving these proteins at different sites. For example, botulinum types A and E both cleave the 25 kiloDalton (kD) synaptosomal associated protein (SNAP-25), but they target different amino acid sequences within this protein. Botulinum toxin types B, D, F and G act on vesicle-associated protein (VAMP, also called synaptobrevin), with each serotype cleaving the protein at a different site. Finally, botulinum toxin type $C_1$ has been shown to cleave both syntaxin and SNAP-25. These differences in mechanism of action may affect the relative potency and/or duration of action of the various botulinum toxin serotypes. Significantly, it is known that the cytosol of pancreatic islet B cells contains at least SNAP-25 (*Biochem J* 1; 339 (pt 1): 159-65 (April 1999)), and synaptobrevin (*Mov Disord* 1995 May; 10(3): 376).

The molecular weight of the botulinum toxin protein molecule, for all seven of the known botulinum toxin serotypes, is about 150 kD. Interestingly, the botulinum toxins are released by *Clostridial bacterium* as complexes comprising the 150 kD botulinum toxin protein molecule along with associated non-toxin proteins. Thus, the botulinum toxin type A complex can be produced by *Clostridial bacterium* as 900 kD, 500 kD and 300 kD forms. Botulinum toxin types B and C, is apparently produced as only a 500 kD complex. Botulinum toxin type D is produced as both 300 kD and 500 kD complexes. Finally, botulinum toxin types E and F are produced as only approximately 300 kD complexes. The complexes (i.e. molecular weight greater than about 150 kD) are believed to contain a non-toxin hemaglutinin protein and a non-toxin and non-toxic nonhemaglutinin protein. These two non-toxin proteins (which along with the botulinum toxin molecule comprise the relevant neurotoxin complex) may act to provide stability against denaturation to the botulinum toxin molecule and protection against digestive acids when toxin is ingested. Additionally, it is possible that the larger (greater than about 150 kD molecular weight) botulinum toxin complexes may result in a slower rate of diffusion of the botulinum toxin away from a site of intramuscular injection of a botulinum toxin complex.

In vitro studies have indicated that botulinum toxin inhibits potassium cation induced release of both acetylcholine and norepinephrine from primary cell cultures of brainstem tissue. Additionally, it has been reported that botulinum toxin inhibits the evoked release of both glycine and glutamate in primary cultures of spinal cord neurons and that in brain synaptosome preparations botulinum toxin inhibits the release of each of the neurotransmitters acetylcholine, dopamine, norepinephrine, CGRP and glutamate.

Botulinum toxin type A can be obtained by establishing and growing cultures of *Clostridium botulinum* in a fermenter and then harvesting and purifying the fermented mixture in accordance with known procedures. All the botulinum toxin serotypes are initially synthesized as inactive single chain proteins which must be cleaved or nicked by proteases to become neuroactive. The bacterial strains that make botulinum toxin serotypes A and G possess endogenous proteases and serotypes A and G can therefore be recovered from bacterial cultures in predominantly their active form. In contrast, botulinum toxin serotypes $C_1$, D and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the botulinum toxin type B serotype only cleave a portion of the toxin produced. The exact proportion of nicked to unnicked molecules depends on the length of incubation and the temperature of the culture. Therefore, a certain percentage of any preparation of, for example, the botulinum toxin type B toxin is likely to be inactive, possibly accounting for the known significantly lower potency of botulinum toxin type B as compared to botulinum toxin type A. The presence of inactive botulinum toxin molecules in a clinical preparation will contribute to the overall protein load of the preparation, which has been linked to increased antigenicity, without contributing to its clinical efficacy. Additionally, it is known that botulinum toxin type B has, upon intramuscular injection, a shorter duration of activity and is also less potent than botulinum toxin type A at the same dose level.

High quality crystalline botulinum toxin type A can be produced from the Hall A strain of *Clostridium botulinum* with characteristics of $\geq 3\times 10^7$ U/mg, an $A_{260}/A_{278}$ of less than 0.60 and a distinct pattern of banding on gel electrophoresis. The known Schantz process can be used to obtain crystalline botulinum toxin type A, as set forth in Schantz, E. J., et al, *Properties and use of Botulinum toxin and Other Microbial Neurotoxins in Medicine,* Microbiol Rev. 56: 80-99 (1992). Generally, the botulinum toxin type A complex can be isolated and purified from an anaerobic fermentation by cultivating *Clostridium botulinum* type A in a suitable medium. The known process can also be used, upon separation out of the non-toxin proteins, to obtain pure botulinum toxins, such as for example: purified botulinum toxin type A with an approximately 150 kD molecular weight with a specific potency of 1-2×10$^8$ LD$_{50}$ U/mg or greater; purified botulinum toxin type B with an approximately 156 kD molecular weight with a specific potency of 1-2×10$^8$ LD$_{50}$ U/mg or greater, and; purified botulinum toxin type F with an approximately 155 kD molecular weight with a specific potency of 1-2×10$^7$ LD$_{50}$ U/mg or greater.

Botulinum toxins and/or botulinum toxin complexes can be obtained from List Biological Laboratories, Inc., Campbell, Calif.; the Centre for Applied Microbiology and Research, Porton Down, U.K.; Wako (Osaka, Japan), Metabiologics (Madison, Wis.) as well as from Sigma Chemicals of St Louis, Mo.

Pure botulinum toxin is so labile that it is generally not used to prepare a pharmaceutical composition. Furthermore. the botulinum toxin complexes, such a the toxin type A complex are also extremely susceptible to denaturation due to surface denaturation, heat, and alkaline conditions. Inactivated toxin forms toxoid proteins which may be immunogenic. The resulting antibodies can render a patient refractory to toxin injection.

As with enzymes generally, the biological activities of the botulinum toxins (which are intracellular peptidases) is dependant, at least in part, upon their three dimensional conformation. Thus, botulinum toxin type A is detoxified by heat, various chemicals surface stretching and surface drying. Additionally, it is known that dilution of the toxin complex obtained by the known culturing, fermentation and purification to the much, much lower toxin concentrations used for pharmaceutical composition formulation results in rapid detoxification of the toxin unless a suitable stabilizing agent is present. Dilution of the toxin from milligram quantities to a solution containing nanograms per milliliter presents significant difficulties because of the rapid loss of specific toxicity upon such great dilution. Since the toxin may be used months or years after the toxin containing pharmaceutical composition is formulated, the toxin must be stabilized with a stabilizing agent. The only successful stabilizing agent for this purpose has been the animal derived proteins albumin and gelatin. And as indicated, the presence of animal derived proteins in the final formulation presents potential problems in that certain stable viruses, prions or other infectious or pathogenic compounds carried through from donors can contaminate the toxin.

Furthermore, any one of the harsh pH, temperature and concentration range conditions required to lyophilize (freeze-dry) or vacuum dry a botulinum toxin containing pharmaceutical composition into a toxin shipping and storage format (ready for use or reconstitution by a physician) can detoxify some of the toxin. Thus, animal derived or donor pool proteins such as gelatin and serum albumin have been used with some success to stabilize botulinum toxin.

A commercially available botulinum toxin containing pharmaceutical composition is sold under the trademark BOTOX® (available from Allergan, Inc., of Irvine, Calif.). BOTOX® consists of a purified botulinum toxin type A complex, albumin and sodium chloride packaged in sterile, vacuum-dried form. The botulinum toxin type A is made from a culture of the Hall strain of *Clostridium botulinum* grown in a medium containing N-Z amine and yeast extract. The botulinum toxin type A complex is purified from the culture solution by a series of acid precipitations to a crystalline complex consisting of the active high molecular weight toxin protein and an associated hemagglutinin protein. The crystalline complex is re-dissolved in a solution containing saline and albumin and sterile filtered (0.2 microns) prior to vacuum-drying. BOTOX® can be reconstituted with sterile, non-preserved saline prior to intramuscular injection. Each vial of BOTOX® contains about 100 units (U) of *Clostridium botulinum* toxin type A purified neurotoxin complex, 0.5 milligrams of human serum albumin and 0.9 milligrams of sodium chloride in a sterile, vacuum-dried form without a preservative.

To reconstitute vacuum-dried BOTOX® sterile normal saline without a preservative; 0.9% Sodium Chloride Injection is used by drawing up the proper amount of diluent in the appropriate size syringe. Since BOTOX® is believed to be denatured by bubbling or similar violent agitation, the diluent is gently injected into the vial. BOTOX® should be administered within four hours after reconstitution. During this time period, reconstituted BOTOX® is stored in a refrigerator (2° to 8° C.). Reconstituted BOTOX® is clear, colorless and free of particulate matter. The vacuum-dried product is stored in a freezer at or below −5° C. BOTOX® is administered within four hours after the vial is removed from the freezer and reconstituted. During these four hours, reconstituted BOTOX® can be stored in a refrigerator (2° to 8° C.). Reconstituted BOTOX® is clear, colorless and free of particulate matter.

It has been reported that botulinum toxin type A has been used in clinical settings as follows:

(1) about 75-125 units of BOTOX® per intramuscular injection (multiple muscles) to treat cervical dystonia;

(2) 5-10 units of BOTOX® per intramuscular injection to treat glabellar lines (brow furrows) (5 units injected intramuscularly into the procerus muscle and 10 units injected intramuscularly into each corrugator supercilii muscle);

(3) about 30-80 units of BOTOX® to treat constipation by intrasphincter injection of the puborectalis muscle;

(4) about 1-5 units per muscle of intramuscularly injected BOTOX® to treat blepharospasm by injecting the lateral pre-tarsal orbicularis oculi muscle of the upper lid and the lateral pre-tarsal orbicularis oculi of the lower lid.

(5) to treat strabismus, extraocular muscles have been injected intramuscularly with between about 1-5 units of BOTOX®, the amount injected varying based upon both the size of the muscle to be injected and the extent of muscle paralysis desired (i.e. amount of diopter correction desired).

(6) to treat upper limb spasticity following stroke by intramuscular injections of BOTOX® into five different upper limb flexor muscles, as follows:
(a) flexor digitorum profundus: 7.5 U to 30 U
(b) flexor digitorum sublimus: 7.5 U to 30 U
(c) flexor carpi ulnaris: 10 U to 40 U
(d) flexor carpi radialis: 15 U to 60 U
(e) biceps brachii: 50 U to 200 U. Each of the five indicated muscles has been injected at the same treatment session, so that the patient receives from 90 U to 360 U of upper limb flexor muscle BOTOX® by intramuscular injection at each treatment session.

(7) to treat migraine, pericranial injected (injected symmetrically into glabellar, frontalis and temporalis muscles) injection of 25 U of BOTOX® has showed significant benefit as a prophylactic treatment of migraine compared to vehicle as measured by decreased measures of migraine frequency, maximal severity, associated vomiting and acute medication use over the three month period following the 25 U injection.

It is known that botulinum toxin type A can have an efficacy for up to 12 months (*European J. Neurology* 6 (Supp 4): S111-S1150:1999, and in some circumstances for as long as 27 months, (*The Laryngoscope* 109: 1344-1346:1999)). However, the usual duration of an intramuscular injection of Botox® is typically about 3 to 4 months.

As set forth, certain botulinum toxins have been used to treat various movement disorders, such as spasmodic muscle conditions with a resulting alleviation of pain. For example, it is known to use a botulinum toxin to treat muscle spasms with resulting relief from both the spasmodic muscle hyperactivity and from the pain which secondarily arises as a result of or due to the spasmodic muscle activity. For example, Cheshire et al *Pain* 1994; 59(1):65-69 reported that patients with myofascial pain syndrome experienced a reduction of pain after injections of botulinum toxin type A to trigger points. See also WO 94/15629. It is believed that botulinum toxin A can reduce pain by reducing the sustained muscle contraction that caused or that substantially caused the pain in the first place. Thus, the pain which can result from or which can accompany a muscle spasm can be due to the lower, local pH caused by the spasm. An indirect effect of the flaccid muscle paralysis induced by a botulinum toxin is to permit the pH to return to a physiological level, thereby causing pain reduction as a secondary effect of the motor endplate cholinergic denervation which can result due to peripheral botulinum toxin administration.

Botulinum toxin can be used to treat migraine headache pain that is associated with muscle spasm, vascular disturbances, neuralgia and neuropathy. Binder U.S. Pat. No. 5,714,468, the disclosure of which is incorporated by its entirety herein by reference. Notably, muscle spasm pain, hypertonic muscle pain, myofascial pain and migraine headache pain can all be due, at least in part, to the production and release of one or more nociceptive substances from the muscles themselves during periods of increased muscle tension or contraction.

The success of botulinum toxin type A to treat a variety of clinical conditions has led to interest in other botulinum toxin serotypes. A study of two commercially available botulinum type A preparations (BOTOX® and Dysport®) and preparations of botulinum toxins type B and F (both obtained from Wako Chemicals, Japan) has been carried out to determine local muscle weakening efficacy, safety and antigenic potential. Botulinum toxin preparations were injected into the head of the right gastrocnemius muscle (0.5 to 200.0 units/kg) and muscle weakness was assessed using the mouse digit abduction scoring assay (DAS). $ED_{50}$ values were calculated from dose response curves. Additional mice were given intramuscular injections to determine $LD_{50}$ doses. The therapeutic index was calculated as $LD_{50}/ED_{50}$. Separate groups of mice received hind limb injections of BOTOX® (5.0 to 10.0 units/kg) or botulinum toxin type B (50.0 to 400.0 units/kg), and were tested for muscle weakness and increased water consumption, the later being a putative model for dry mouth. Antigenic potential was assessed by monthly intramuscular injections in rabbits (1.5 or 6.5 ng/kg for botulinum toxin type B or 0.15 ng/kg for BOTOX®). Peak muscle weakness and duration were dose related for all serotypes. DAS $ED_{50}$ values (units/kg) were as follows: BOTOX®: 6.7, Dysport®: 24.7, botulinum toxin type B: 27.0 to 244.0, botulinum toxin type F: 4.3. BOTOX® had a longer duration of action than botulinum toxin type B or botulinum toxin type F. Therapeutic index values were as follows: BOTOX®: 10.5, Dysport®: 6.3, botulinum toxin type B: 3.2. Water consumption was greater in mice injected with botulinum toxin type B than with BOTOX®, although botulinum toxin type B was less effective at weakening muscles. After four months of injections 2 of 4 (where treated with 1.5 ng/kg) and 4 of 4 (where treated with 6.5 ng/kg) rabbits developed antibodies against botulinum toxin type B. In a separate study, 0 of 9 BOTOX® treated rabbits demonstrated antibodies against botulinum toxin type A. DAS results indicate relative peak potencies of botulinum toxin type A being equal to botulinum toxin type F, and botulinum toxin type F being greater than botulinum toxin type B. With regard to duration of effect, botulinum toxin type A was greater than botulinum toxin type B, and botulinum toxin type B duration of effect was greater than botulinum toxin type F. As shown by the therapeutic index values, the two commercial preparations of botulinum toxin type A (BOTOX® and Dysport®) are different. The increased water consumption behavior observed following hind limb injection of botulinum toxin type B indicates that clinically significant amounts of this serotype entered the murine systemic circulation. The results also indicate that in order to achieve efficacy comparable to botulinum toxin type A, it is necessary to increase doses of the other serotypes examined. Increased dosage can comprise safety. Furthermore, in rabbits, type B was more antigenic than was BOTOX®, possibly because of the higher protein load injected to achieve an effective dose of botulinum toxin type B. *Eur J Neurol* 1999 November; 6(Suppl 4):S3-S10.

In addition to having pharmacologic actions at the peripheral location, botulinum toxins may also have inhibitory effects in the central nervous system. Work by Weigand et al, *Naunyn-Schmiedeberg's Arch. Pharmacol.* 1976; 292, 161-165, and Habermann, *Naunyn-Schmiedeberg's Arch. Pharmacol.* 1974; 281, 47-56 showed that botulinum toxin is able to ascend to the spinal area by retrograde transport. As such, a botulinum toxin injected at a peripheral location, for example intramuscularly, may be retrograde transported to the spinal cord. However, the authors of the cited articles were unable to demonstrate that the radioalabelled material was intact botulinum toxin.

As discussed above, pain associated with muscle disorder, for example muscle spasm pain, and headache pain associated with vascular disturbances, neuralgia and neuropathy may be effectively treated by the use of botulinum toxin. However, there is a clear deficiency in available means for the treatment of an array of other types of pain. Such pain include, for example, pain not associated with muscle disorder, non-headache neuralgia and neuropathy pain, tissue inflammation pain, joint inflammation pain, tissue inflammation pain, cancer pain, post-operational pain, laceration pain, ischemic pain, etc.

Attempts have been made to address these other types of pain, but their potential success and possible clinical use is uncertain at this time. For example, Foster et al. in U.S. Pat. No. 5,989,545 (incorporated herein by reference in its entirety) disclose that a *Clostridial* neurotoxin, preferably a botulinum toxin, chemically conjugated or recombinantly fused to a particular targeting moiety can be used to treat pain.

Acetylcholine

Typically only a single type of small molecule neurotransmitter is released by each type of neuron in the mammalian nervous system. The neurotransmitter acetylcholine is secreted by neurons in many areas of the brain, but specifically by the large pyramidal cells of the motor cortex, by several different neurons in the basal ganglia, by the motor neurons that innervate the skeletal muscles, by the preganglionic neurons of the autonomic nervous system (both sympathetic and parasympathetic), by the postganglionic neurons of the parasympathetic nervous system, and by some of the postganglionic neurons of the sympathetic nervous system. Essentially, only the postganglionic sympathetic nerve fibers to the sweat glands, the piloerector muscles and a few blood vessels are cholinergic as most of the postganglionic neurons of the sympathetic nervous system secret the neurotransmitter norepinephine. In most instances acetylcholine has an excitatory effect. However, acetylcholine is known to have inhibitory effects at some of the peripheral parasympathetic nerve endings, such as inhibition of heart rate by the vagal nerve.

The efferent signals of the autonomic nervous system are transmitted to the body through either the sympathetic nervous system or the parasympathetic nervous system. The preganglionic neurons of the sympathetic nervous system extend from preganglionic sympathetic neuron cell bodies located in the intermediolateral horn of the spinal cord. The preganglionic sympathetic nerve fibers, extending from the cell body, synapse with postganglionic neurons located in either a paravertebral sympathetic ganglion or in a prevertebral ganglion. Since, the preganglionic neurons of both the sympathetic and parasympathetic nervous system are cholinergic, application of acetylcholine to the ganglia will excite both sympathetic and parasympathetic postganglionic neurons.

Acetylcholine activates two types of receptors, muscarinic and nicotinic receptors. The muscarinic receptors are found in all effector cells stimulated by the postganglionic neurons of the parasympathetic nervous system, as well as in those stimulated by the postganglionic cholinergic neurons of the sympathetic nervous system. The nicotinic receptors are found in the synapses between the preganglionic and postganglionic neurons of both the sympathetic and parasympathetic. The nicotinic receptors are also present in many membranes of skeletal muscle fibers at the neuromuscular junction.

Acetylcholine is released from cholinergic neurons when small, clear, intracellular vesicles fuse with the presynaptic neuronal cell membrane. A wide variety of non-neuronal secretory cells, such as, adrenal medulla (as well as the PC12 cell line) and pancreatic islet cells release catecholamines and parathyroid hormone, respectively, from large dense-core vesicles. The PC12 cell line is a clone of rat pheochromocytoma cells extensively used as a tissue culture model for studies of sympathoadrenal development. Botulinum toxin inhibits the release of both types of compounds from both types of cells in vitro, permeabilized (as by electroporation) or by direct injection of the toxin into the denervated cell. Botulinum toxin is also known to block release of the neurotransmitter glutamate from cortical synaptosomes cell cultures.

A neuromuscular junction is formed in skeletal muscle by the proximity of axons to muscle cells. A signal transmitted through the nervous system results in an action potential at the terminal axon, with activation of ion channels and resulting release of the neurotransmitter acetylcholine from intraneuronal synaptic vesicles, for example at the motor endplate of the neuromuscular junction. The acetylcholine crosses the extracellular space to bind with acetylcholine receptor proteins on the surface of the muscle end plate. Once sufficient binding has occurred, an action potential of the muscle cell causes specific membrane ion channel changes, resulting in muscle cell contraction. The acetylcholine is then released from the muscle cells and metabolized by cholinesterases in the extracellular space. The metabolites are recycled back into the terminal axon for reprocessing into further acetylcholine What is needed therefore is an effective, long lasting, non-surgical method to treat pain, particularly pain which is not associated with a muscle disorder or headache.

SUMMARY

The present invention meets this need and provides an effective, long lasting, non-surgical method to treat pain, particularly pain which is not associated with a muscle disorder or headache.

A method within the scope of the present invention for treating pain can comprise the step of peripheral administration of a neurotoxin to a mammal. The pain treated is not associated with a muscle disorder, such as a muscle spasm, because it is believed that a mechanism by which the present invention works is by an antinociceptive effect upon peripheral, sensory afferent pain neurons, as opposed to having an effect upon motor neurons.

The neurotoxin can comprise a neuronal binding moiety which is substantially native to the neurotoxin. The neurotoxin can be a botulinum toxin, such as one of the botulinum toxin types A, B, $C_1$, D, E, F or G. Preferably the botulinum toxin is botulinum toxin type A.

The neurotoxin can be a modified neurotoxin which has at least one amino acid deleted, modified or replaced. Additionally, the neurotoxin can be made at least in part by a recombinant process.

The neurotoxin can be administered in an amount between about 0.01 U/kg and about 35 U/kg and the pain treated can be substantially alleviated for between about 1 month and about 27 months, for example for from about 1 month to about 6 months.

The peripheral administration of the neurotoxin can be carried out prior to an onset of a nociceptive event or syndrome experienced by a patient. Additionally, the peripheral administration of the neurotoxin can be carried out subsequent to an onset of a nociceptive event experienced by a patient.

A detailed embodiment of a method within the scope of the present invention can comprise the step of peripheral administration of a botulinum toxin to a human patient, thereby alleviating pain, wherein the pain is not associated with a muscle spasm or with a headache.

A further method within the scope of the present invention can comprise the step of peripheral administration of a neurotoxin to a mammal, wherein the neurotoxin is a polypeptide comprising: (a) a first amino acid sequence region comprising a wild type neuronal binding moiety, substantially completely derived from a neurotoxin selected from a group consisting botulinum toxin types A, B, $C_1$, D, E, F, G and mixtures thereof; (b) a second amino acid sequence region effective to translocate the polypeptide or a part thereof across an endosome membrane, and; (c) a third amino acid sequence region having therapeutic activity when released into a cytoplasm of a target cell, wherein the pain is not associated with a muscle spasm.

The first amino acid sequence region of the polypeptide can comprise a carboxyl terminal of a heavy chain derived from the neurotoxin and the neurotoxin can be a botulinum toxin, such as botulinum toxin type A.

The second amino acid sequence region of the polypeptide can have an amine terminal of a heavy chain derived from a neurotoxin selected from a group consisting of botulinum toxin types A, B, $C_1$, D, E, F, G and mixtures thereof. Notably, the second amino acid sequence region of the polypeptide can include an amine terminal of a toxin heavy chain derived from botulinum toxin type A.

Finally, the third amino acid sequence region of the polypeptide can comprise a toxin light chain derived from a neurotoxin selected from a group consisting of *Clostridium beratti* toxin; *butyricum* toxin; *tetani* toxin; botulinum toxin types A, B, $C_1$, D, E, F, G and mixtures thereof. The third amino acid sequence region of the polypeptide can include a toxin light chain derived from botulinum toxin type A.

The present invention also includes a method for improving patient function, the method comprising the step of peripheral administration of a botulinum toxin to a patient experiencing a non-muscle disorder related pain, thereby improving patient function as determined by improvement in one or more of the factors of reduced pain, reduced time spent in bed, improve hearing, increased ambulation, healthier attitude and a more varied lifestyle.

Significantly, the neurotoxins within the scope of the present invention comprise a native or wild type binding moiety with a specific affinity for a neuronal cell surface receptor. The neurotoxins within the scope of the present invention exclude neuronal targeting moieties which are not native to the neurotoxin because we have found that the present invention can be effectively practiced without the necessity of making any modification or deletions to the native or wild type binding moiety of the neurotoxins used.

Thus, use of a neurotoxin with one or more non-native, targeting moiety artifacts or constructs is excluded from the scope of the present invention as unnecessary because, as stated, we have surprisingly discovered that peripheral administration of a neurotoxin according to the present invention provides significant pain alleviation even though the neurotoxin does not comprise a non-native neuronal targeting moiety. Thus we have discovered that a neurotoxin, such as botulinum toxin type A, can upon peripheral administration provide alleviation of pain even though the neurotoxin has not been artificially or manipulatively accorded any attachment of a non-native neuronal targeting moiety.

Surprisingly, we have discovered that a neurotoxin, for example a *Clostridial* neurotoxin, having a wild type neuronal binding moiety can be peripherally administered into a mammal to treat pain. The wild type neuronal binding moiety is originally part of the neurotoxin. For example, botulinum toxin type A, with its original wild type neuronal binding moiety can be administered peripherally in amounts between about 0.01 U/kg to about 35 U/kg to alleviate pain experienced by a mammal, such as a human patient. Preferably, the botulinum toxin used is peripherally administered in an amount between about 0.1 U/kg to about 3 U/kg. Significantly, the pain alleviating effect of the present disclosed methods can persist for an average of 1-6 months and longer in some circumstances. It has been reported that an effect of a botulinum toxin can persist for up to 27 months after administration.

In another embodiment, the method of treating pain comprises administering to a mammal a neurotoxin, for example a *Clostridial* neurotoxin, wherein the neurotoxin differs from a naturally occurring neurotoxin by at least one amino acid. The neurotoxin also has a wild type neuronal binding moiety.

In another embodiment, the methods of treating pain comprises administering to a mammal a neurotoxin, for example a *Clostridial* neurotoxin, wherein the neurotoxin has a wild type neuronal binding moiety of another neurotoxin subtype.

The present invention also includes a method for treating a post-operative pain where the pain is a result of the surgical procedure carried out (i.e. the pain is due, at least in part, to the incisions made). The method can comprise the step of peripheral administration of an effective amount of a botulinum toxin before (i.e. up to 10 days before the surgery), during or immediately after (i.e. by no later than about 6-12 hours after the surgery) a surgical procedure, thereby alleviating or significantly alleviating a post-operative pain. The scope of our invention does not include a method wherein the surgical procedure is carried out to treat a muscle spasm.

Our invention also includes a method for treating a visceral pain by a non-systemic, local administration of an effective amount of a botulinum toxin to thereby alleviate the visceral pain. A visceral pain is a pain which is perceived by the patient to arise from a site in the viscera, that is in an organ of the digestive, respiratory, urogenital, and endocrine systems, as well in the spleen, heart and/or vessels. Thus, visceral pain includes pain in the pancreas, intestine, stomach and abdominal muscles.

A preferred method within the scope of the present invention for treating pain comprises the step of peripheral administration of a neurotoxin to a mammal. The pain treated is not substantially due to a muscle spasm because we have surprisingly discovered that a neurotoxin within the scope of the present invention can be used to treat pain which is not secondary to a muscle spasm. Thus, the present invention is applicable to the treatment of pain which arises irrespective of the present or absence of a muscle disorder, such as a muscle spasm. Additionally, the present invention is also applicable to and includes within its scope, the treatment of pain which is not secondary to a muscle spasm. Thus, a patient can have a spasmodic or hypertonic muscle and also experience pain which is not secondary, that is does not arise from or is not due to, to the muscle spasm. For example, a patient can have a spasmodic limb muscle and concurrently experience pain in the truck, such as a back pain. In this example, a method within the scope of the present invention can treat the back pain by peripheral (i.e. subcutaneous) administration of a neurotoxin to the patient's back.

Definitions

The following definitions are provided and apply herein:

"Light chain" means the light chain of a clostridial neurotoxin. It can have a molecular weight of about 50 kDa, and can be referred to as L chain, L or as the proteolytic domain (amino acid sequence) of a clostridial neurotoxin.

"Heavy chain" means the heavy chain of a clostridial neurotoxin. It can have a molecular weight of about 100 kDa and can be referred to herein as H chain or as H.

"$H_N$" means a fragment which can have a molecular weight of about 50 kDa, is derived from the H chain of a *Clostridial* neurotoxin and is approximately equivalent to the amino terminal segment of the H chain, or the portion corresponding to that fragment in the intact in the H chain. It is believed to contain the portion of the natural or wild type clostridial neurotoxin involved in the translocation of the L chain across an intracellular endosomal membrane.

"$H_C$" means a fragment (about 50 kDa) derived from the H chain of a clostridial neurotoxin which is approximately equivalent to the carboxyl terminal segment of the H chain, or the portion corresponding to that fragment in the intact H chain. It is believed to be immunogenic and to contain the portion of the natural or wild type *Clostridial* neurotoxin involved in high affinity, presynaptic binding to motor neurons.

"Wild type neuronal binding moiety" means that portion of a neurotoxin which is native to the neurotoxin and which exhibits a specific binding affinity for a receptor on a neuron. Thus, wild type or native neuronal binding moiety excludes a binding moiety with is not native to the neurotoxin.

"Targeting moiety" means a molecule that has a specific binding affinity for a cell surface receptor. The targeting moiety is not a *Clostridial* neurotoxin $H_C$, or peptides derived from $H_C$ with at least one of its amino acid deleted, modified or replaced. The targeting moiety is a molecule which is not a *Clostridial* neurotoxin, for example can be a bradykinin.

"Local administration" means administration by a non-systemic route at or in the vicinity of the site of an affliction, disorder or perceived pain.

"Peripheral administration" means administration by means of a non-systemic route to a peripheral location on a mammal. A peripheral location generally means, under the skin or into a skeletal muscle. Peripheral administration includes peripheral intramuscular, intraglandular, and subcutaneous administration routes, but excludes intravenous or oral administration and further excludes any direct administration to the central nervous system.

DRAWINGS

These and other features, aspects, and advantages of the present invention can become better understood from the following description, claims and the accompanying drawings, where in FIGS. 1 and 2 below, "injection" means peripheral injection or administration.

FIG. 1 is a dose response graph showing that a method within the scope of the present invention alleviates induced inflammatory pain under the rat formalin model for at least five days. The X axis sets forth time in minutes after commencement of the formalin model in rats. The Y axis sets forth time spent lifting and licking the formalin injected paw upon use of control (saline, n=7) and BOTOX® (botulinum toxin type A purified neurotoxin complex) injections at concentrations of 7 U/kg (n=8), 15 U/kg (n=5) and 30 U/kg (n=4). The BOTOX® was injected 5 days before commencement of the formalin challenge.

Figure 2:
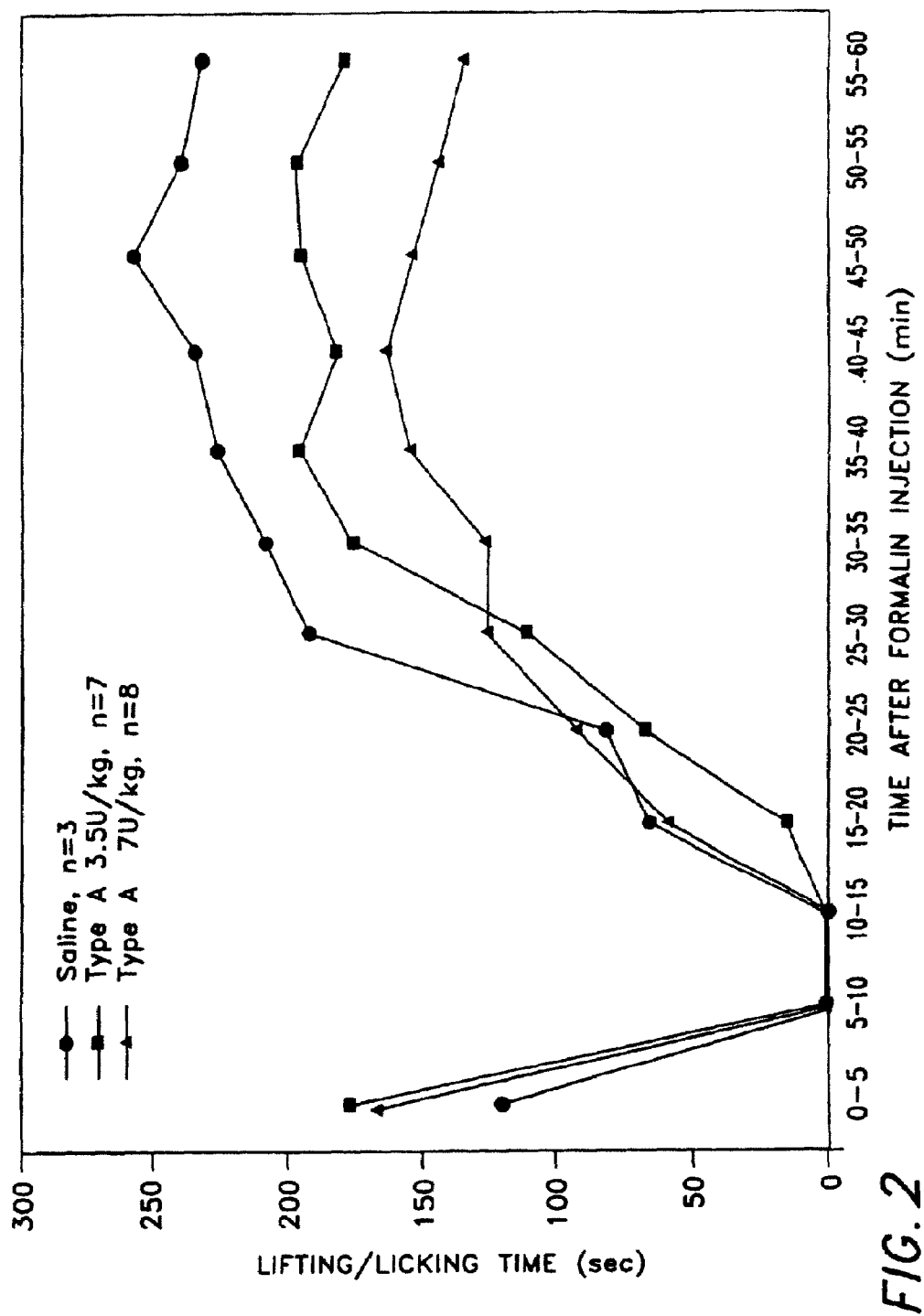

FIG. 2 is a dose response graph showing that a method within the scope of the present invention alleviates induced inflammatory pain under the rat formalin model for at least twelve days. The X axis sets forth time in minutes after commencement of the formalin model in rats. The Y axis sets forth time spent lifting and licking the formalin injected paw upon use of control (saline, n=3) and BOTOX® (botulinum toxin type A purified neurotoxin complex) injections at concentrations of 3.5 U/kg (n=7) and 7 U/kg (n=8). The BOTOX® was injected 12 days before commencement of the formalin challenge.

DESCRIPTION

The present invention is based on the discovery that peripheral administration of a neurotoxin can provide effective treatment of chronic pain. Notably, the neurotoxin has a wild type or native neuronal binding moiety. The pain treated is not due to a muscle spasm, nor is the pain headache pain. Chronic pain is treated because of the long term antinociceptive effect of the neurotoxins used. The neuronal binding moiety component of the neurotoxin is a neuronal binding moiety which is native to the selected neurotoxin because we have discovered that the present invention can be practiced without replacement of the wild type neuronal binding moiety with a non-native or non wild type targeting moiety. Treatment of headache pain is not within the scope of the present invention because the preferred sites of peripheral administration of a neurotoxin according to the present invention exclude the head and neck.

Prior to our discovery a neurotoxin, such as a botulinum toxin, has been used to treat pain associated with various muscle disorders. Thus, it is known that a muscle disorder, such as a spasmodic muscle, can cause pain and that by treating the spasm the pain can also be alleviated. Foster et al. discloses that the neurotoxin be linked to a targeting moiety for use in the treatment of pain, that is that the wild type binding moiety of a *Clostridial* neurotoxin be removed completely, and replaced by a targeting moiety.

Surprising we have discovered that a neurotoxin which has not been conjugated, attached, adhered to or fused with a neuronal targeting moiety can be peripherally administered according to the methods of the present invention to treat pain. Preferably, the pain treated is not due, that is the pain does not directly arise from as a secondary result of, a muscle spasm. Our invention can be used to treat pain which results from a wide variety of neuropathic, inflammatory, cancerous and trauma conditions.

Prior to our invention is was not known that a neurotoxin, such as a botulinum toxin, could be used to effectively treat pain, where the pain is not due to a muscle spasm or hypertonic muscle condition. The physiological mechanism by which peripheral administration of a neurotoxin can result in long term alleviation of pain is unclear. We note that whereas the pain due to a muscle spasm or hypertonic muscle condition can produce a reduced, local pH, our invention does not rest upon and does not require elevation of a local, low pH level. Additionally, whereas a muscle spasm or hypertonic muscle condition can be alleviated by an anticholinergic effect of a neurotoxin, such as a botulinum toxin, upon motor neurons, our invention is not predicated upon an effect upon motor neurons. Without wishing to be bound by theory, we hypothesize, that one effect of peripheral administration of a neurotoxin, such as a botulinum toxin, according to the present invention can be an antinociceptive effect upon a peripheral, sensory afferent neuron. Significantly, in our invention pain alleviation is a primary, as opposed to being a secondary, effect upon peripheral administration of a neurotoxin, such as a botulinum toxin.

Thus, the present invention is based, at least in part, upon the discovery that a neurotoxin having a wild type neuronal binding moiety may be peripherally administered to a mammal to alleviate pain. The neurotoxin according to this invention is not coupled to a non-native targeting moiety. A wild type binding moiety according to the present invention can be a naturally existing $H_C$ segment of a *Clostridial* neurotoxin or an amino acid sequence substantially completely derived from the $H_C$ segment of the *Clostridial* neurotoxin.

As used hereinafter, an amino acid sequence, for example a wild type binding moiety, "derived from" another amino acid sequence, for example the $H_C$ segment, means that the resultant amino acid sequence is duplicated exactly like the amino acid sequence from which it is derived; or the resultant amino acid sequence has at least one amino acid deleted, modified or replaced as compared to the amino acid sequence from which it is derived.

According to one broad aspect of the invention, there are provided methods for treatment of pain which comprise administering to a mammal effective doses of a neurotoxin, for example a *Clostridial* neurotoxin, having a wild type neuronal binding moiety. In one embodiment, the methods include administering to a mammal a neurotoxin having a wild type neuronal binding moiety which is originally already a part of the neurotoxin. For example, such neurotoxin may be selected from a group consisting of *beratti* toxin and *butyricum* toxin, each of which already has a neuronal binding moiety. The neurotoxin may also be a *tetani* toxin, which also has a wild type neuronal binding moiety. Preferably, the neurotoxin administered to the mammal is selected from a group consisting of botulinum toxin types A, B, $C_1$, D, E, F, or G, each of which has its own original wild type neuronal binding moiety. More preferably, the methods include the administration of botulinum type A with its original wild type neuronal binding moiety. The methods also include the administration of a mixture of two or more of the above neurotoxins to a mammal to treat pain.

In another embodiment, the methods comprise the administration of a neurotoxin, for example a *Clostridial* neurotoxin, to a mammal wherein the neurotoxin differs from a naturally occurring neurotoxin by at least one amino acid. For example, variants of botulinum toxin type A as disclosed in Biochemistry 1995, 34, pages 15175-15181 and Eur. J. Biochem, 1989, 185, pages 197-203 (incorporated herein by reference in its entirety) may be administered to a mammal to treat non-spasm related pain. These variants also have wild type neuronal binding moieties.

In another embodiment, methods are provided for an administration of a neurotoxin to a mammal to treat non-spasm caused pain, wherein the neurotoxin has a wild type neuronal binding moiety of another neurotoxin. For example, the method includes the step of administering to a mammal botulinum toxin type A having a wild type neuronal binding moiety of botulinum toxin type B. All other such combinations are included within the scope of the present invention.

In another broad embodiment, methods of the present invention to treat non-spasm related pain include local, peripheral administration of the neurotoxin to an actual or a perceived pain location on the mammal. In one embodiment, the neurotoxin is administered subcutaneously at or near the location of the perceived pain, for example at or near a chronically painful joint. In another embodiment, the neurotoxin is administered intramuscularly at or near the location of pain, for example at or near a neoplasm on the mammal. In another embodiment, the neurotoxin is injected directly into a joint of a mammal, for treating or alleviating pain causing arthritic conditions. Also, frequent, repeated injections or infusion of the neurotoxin to a peripheral pain location is within the scope of the present invention. However, given the long lasting therapeutic effects of the present invention, frequent injections or infusion of the neurotoxin may not be necessary. For example, practice of the present invention can provide an analgesic effect, per injection, for 2 months or longer, for example 7 months, in humans.

Without wishing to limit the invention to any mechanism or theory of operation, it is believed that when the neurotoxin is administered locally to a peripheral location, it inhibits the release of neuro-substances, for example substance P, from the peripheral primary sensory terminal. As discussed above, a release of substance P by the peripheral primary sensory terminal may cause or at least amplify pain transmission process. Therefore, inhibition of its release at the peripheral primary sensory terminal will dampen the pain transmission process.

In addition to having pharmacologic actions at a peripheral location of administration, a method within the scope of the present invention may also have an antinociceptive effect due to retrograde transport to the neurotoxin from the site of peripheral (i.e. subcutaneous) injection to the central nervous system. We have determined that botulinum type A can be retrograde transported from the peripheral site of administration back to the dorsal horn of the spinal cord. Presumably the retrograde transport is via the primary afferent. This finding is consistent with the work by Weigand et al, Naunyn-Schmiedeberg's Arch. Pharmacol. 1976; 292,161-165, and Habermann, Naunyn-Schmiedeberg's Arch. Pharmacol. 1974; 281, 47-56, which showed that botulinum toxin is able to ascend to the spinal area by retrograde transport. Thus, it was reported that botulinum toxin type A injected intramuscularly may be retrograde transported from the peripheral primary sensory terminal to the central primary sensory terminal.

Our discovery differs significantly from the discussion in the articles cited in the paragraph above. We have discovered that, in the rat, after peripheral, subcutaneous administration botulinum toxin was found localized in the animal's dorsal horn, that is at the location where the C fibers synapse. A subcutaneous injection is an injection at a location where many bipolar nociceptive nerve fibers are located. These sensory fibers run from the periphery to the dorsal horn of the spinal cord. Contrarily, in one or more of the articles cited in the paragraph above after intramuscular toxin injection was carried out some radioalabelled botulinum toxin was found localized in the ventral roots. The ventral root of the spinal cord is where monopolar efferent (traffic out) motor neurons are located. Thus, the art leads to an expectation that peripheral muscle spasticity can be expected as a result of retrograde transport of a botulinum toxin from the periphery to a spinal cord location.

Thus, it had been believed by those skilled in the art that the appearance of a neurotoxin, such as a botulinum toxin in the spinal cord of a mammal would: (1) induce significant spasticity in the recipient, and; (2) promote detrimental effects upon spinal cord and brain functions. Thus, with regard to cited deleterious effect (1): it was reported, as examples, in Williamson et al., in *Clostridial Neurotoxins and Substrate Proteolysis in Intact Neurons,* J. of Biological Chemistry 271:13; 7694-7699 (1996) that both tetanus toxin and botulinum toxin type A inhibit the evoked release of the neurotransmitters glycine and glutamate from fetal mice spinal cord cell cultures, while it was reported by Hagenah et al., in *Effects of Type A Botulinum Toxin on the Cholinergic Transmission at Spinal Renshaw Cells and on the Inhibitory Action at Ia Inhibitory Interneurones,* Naunyn-Schmiedeberg's Arch. Pharmacol. 299, 267-272 (1977), that direct intraspinal injection of botulinum toxin type A in experimentally prepared, anaesthetized cats inhibits CNS Renshaw cell activity. Inhibition of central glycine and glutamate neurotransmitter release as well as the downregulation of Renshaw cell activity presumably can both result in vivo in the promotion of significant motorneuron hyperactivity with ensuing peripheral muscle spasticity.

With regard to deleterious effect (2): it is believed that central (spinal cord) presence of a tetanus neurotoxin exerts, by retrograde movement of the tetanus toxin along CNS neurons, significant negative effects upon spinal cord and brain functions, thereby contraindicating any desire to have a related neurotoxin, such as a botulinum toxin appear (as by retrograde transport) in the spinal cord. Notably, botulinum toxin and tetanus toxin are both made by *Clostridial* bacteria, although by different species of *Clostridium.* Significantly, some researchers have reported that botulinum toxin shares, at least to some extent, the noted neural ascent characteristic of tetanus toxin. See e.g. Habermann E., $^{125}$*I-Labeled Neurotoxin from Clostridium Botulinum A: Preparation, Binding to Synaptosomes and Ascent in the Spinal Cord,* Naunyn-Schmiedeberg's Arch. Pharmacol. 281, 47-56 (1974).

Our invention surprisingly encounters neither of the deleterious effects (1) or (2), and the disclosed peripheral (subcutaneous) administration methods of the present invention can be practiced to provide effective and long lasting relief from pain which is not due to a muscle spasm and to provide a general improvement in the quality of life experienced by the treated patient. The pain experienced by the patient can be due, for example, to injury, surgery, infection, accident or disease (including cancer and diabetes), including neuropathic diseases and disorders, where the pain is not primarily due to a muscle spasm or hypertonic muscle condition.

Once in the central primary sensory terminal located in the dorsal horn of the spinal chord, the neurotoxin may further inhibit the release of the neurotransmitter responsible for the transmission of pain signals, for example substance P. This inhibition prevents the activation of the projection neurons in the spinothalamic tract and thereby alleviating pain. Therefore, the peripheral administration of the neurotoxin, due to its now discovered central antinociceptive effect, serve as an alternative method to central (i.e. intraspinal) administration of an analgesic, thereby eliminating the complications associated with central administration of an analgesic drug.

Furthermore, it has been shown by Habermann *Experientia* 1988; 44:224-226 that botulinum toxin can inhibit the release of noradrenalin and GABA from brain homogenates. This finding suggests that botulinum toxin can enter into the adrenergic sympathetic nerve terminals and GABA nerve terminals. As such, botulinum toxin can be administered to the sympathetic system to provide long term block and alleviate pain, for example neuropathic pain. The administration a neurotoxin, preferably botulinum toxin type A, provides a benefit of long term block without the risk of permanent functional impairment, which is not possible with pharmaceutics currently in use.

The amount of the neurotoxin administered can vary widely according to the particular disorder being treated, its severity and other various patient variables including size, weight, age, and responsiveness to therapy. For example, the extent of the area of peripheral pain is believed to be proportional to the volume of neurotoxin injected, while the quantity of the analgesia is, for most dose ranges, believed to be proportional to the concentration of neurotoxin injected. Furthermore, the particular location for neurotoxin administration can depend upon the location of the pain to be treated.

Generally, the dose of neurotoxin to be administered will vary with the age, presenting condition and weight of the mammal to be treated. The potency of the neurotoxin will also be considered.

In one embodiment according to this invention, the therapeutically effective doses of a neurotoxin, for example botulinum toxin type A, at a peripheral location can be in amounts between about 0.01 U/kg and about 35 U/kg. A preferred range for administration of a neurotoxin having a wild type neuronal binding moiety, such as the botulinum toxin type A, so as to achieve an antinociceptive effect in the patient treated is from about 0.01 U/kg to about 35 U/kg. A more preferred range for peripheral administration of a neurotoxin, such as botulinum toxin type A, so as to achieve an antinociceptive effect in the patient treated is from about 1 U/kg to about 15 U/kg. Less than about 0.1 U/kg can result in the desired therapeutic effect being of less than the optimal or longest possible duration, while more than about 2 U/kg can still result in some symptoms of muscle flaccidity. A most preferred range for peripheral administration of a neurotoxin, such as the botulinum toxin type A, so as to achieve an antinociceptive effect in the patient treated is from about 0.1 U/kg to about 1 U/kg.

Although examples of routes of administration and dosages are provided, the appropriate route of administration and dosage are generally determined on a case by case basis by the attending physician. Such determinations are routine to one of ordinary skill in the art (see for example, *Harrison's Principles of Internal Medicine* (1998), edited by Anthony Fauci et al., 14$^{th}$ edition, published by McGraw Hill). For example, the route and dosage for administration of a neurotoxin according to the present disclosed invention can be selected based upon criteria such as the solubility characteristics of the neurotoxin chosen as well as the intensity of pain perceived.

In another broad embodiment of the invention, there are provided methods for treating non-spasm related pain which comprises administering effective doses of a neurotoxin, wherein the neurotoxin is a single polypeptide as opposed to a di-polypeptide as described above.

In one embodiment, the neurotoxin is a single polypeptide having three amino acid sequence regions. The first amino acid sequence region includes a neuronal binding moiety which is substantially completely derived from a neurotoxin selected from a group consisting of *beratti* toxin; *butyricum* toxin; *tetani* toxin; botulinum toxin types A, B, $C_1$, D, E, F, and G. Preferably, the first amino acid sequence region is derived from the carboxyl terminal of a toxin heavy chain, $H_C$. More preferably, the first amino acid sequence region is derived from the $H_C$ of botulinum toxin type A.

The second amino acid sequence region is effective to translocate the polypeptide or a part thereof across an endosome membrane into the cytoplasm of a neuron. In one embodiment, the second amino acid sequence region of the polypeptide comprises an amine terminal of a heavy chain, $H_N$, derived from a neurotoxin selected from a group consisting of *beratti* toxin; *butyricum* toxin; *tetani* toxin; botulinum toxin types A, B, $C_1$, D, E, F, and G. Preferably, the second amino acid sequence region of the polypeptide comprises an amine terminal of a toxin heavy chain, $H_N$, derived botulinum toxin type A.

The third amino acid sequence region has therapeutic activity when it is released into the cytoplasm of a target cell or neuron. In one embodiment, the third amino acid sequence region of the polypeptide comprises a toxin light chain, L, derived from a neurotoxin selected from a group consisting of *beratti* toxin; *butyricum* toxin; *tetani* toxin; botulinum toxin types A, B, $C_1$, D, E, F, and G. Preferably, the third amino acid sequence region of the polypeptide comprises a toxin light chain, L, derived from botulinum toxin type A.

In one embodiment, the polypeptide comprises a first amino acid sequence region derived from the $H_C$ of the *tetani* toxin, a second amino acid sequence region derived from the $H_N$ of botulinum toxin type B, and a third amino acid sequence region derived from the L chain of botulinum type A. In a preferred embodiment, the polypeptide comprises a first amino acid sequence region derived from the $H_C$ of the botulinum toxin type B, a second amino acid sequence region derived from the $H_N$ of botulinum toxin type A, and a third amino acid sequence region derived from the L chain of botulinum type A. All other such combinations are included within the scope of the present invention.

In another embodiment, the polypeptide comprises a first amino acid sequence region derived from the $H_C$ of the botulinum toxin type A, wherein the amino acid sequence has at least one amino acid deleted, modified or replace; a second amino acid sequence region derived from the $H_N$ of botulinum toxin type A, and a third amino acid sequence region derived from the L chain of botulinum type A. All other such combinations are included within the scope of the present invention.

As indicated above, these polypeptides are single chains and may not be as potent as desired. To increase their potency, the third amino acid sequence region may be cleaved off by a proteolytic enzyme, for example a trypsin. The independent third amino acid sequence region may be reattached to the original polypeptide by a disulfide bridge. In one embodiment, the third amino acid sequence region is reattached the original polypeptide at the first amino acid sequence region. In a preferred embodiment, the third amino acid sequence region is reattached to the second amino acid sequence region.

If an unmodified neurotoxin is to be used to treat non-spasm related pain as described herein, the neurotoxin may be obtained by culturing an appropriate bacterial species. For example, botulinum toxin type A can be obtained by establishing and growing cultures of *Clostridium botulinum* in a fermenter and then harvesting and purifying the fermented mixture in accordance with known procedures. All the botulinum toxin serotypes are initially synthesized as inactive single chain proteins which must be cleaved or nicked by proteases to become neuroactive. The bacterial strains that make botulinum toxin serotypes A and G possess endogenous proteases and serotypes A and G can therefore be recovered from bacterial cultures in predominantly their active form. In contrast, botulinum toxin serotypes $C_1$, D and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the botulinum toxin type B serotype only cleave a portion of the toxin produced. The exact proportion of nicked to unnicked molecules depends on the length of incubation and the temperature of the culture. Therefore, a certain percentage of any preparation of, for example, the botulinum toxin type B toxin is likely to be inactive, possibly accounting for the known significantly lower potency of botulinum toxin type B as compared to botulinum toxin type A. The presence of inactive botulinum toxin molecules in a clinical preparation will contribute to the overall protein load of the preparation, which has been linked to increased antigenicity, without contributing to its clinical efficacy. Additionally, it is known that botulinum toxin type B has, upon intramuscular injection, a shorter duration of activity and is also less potent than botulinum toxin type A at the same dose level.

If a modified neurotoxin is to be used according to this invention to treat non-spasm related pain, recombinant techniques can be used to produce the desired neurotoxins. The technique includes steps of obtaining genetic materials from natural sources, or synthetic sources, which have codes for a neuronal binding moiety, an amino acid sequence effective to translocate the neurotoxin or a part thereof, and an amino acid sequence having therapeutic activity when released into a cytoplasm of a target cell, preferably a neuron. In a preferred embodiment, the genetic materials have codes for the $H_C$, $H_N$ and L chain of the *Clostridial* neurotoxins, modified clostridial neurotoxins and fragments thereof. The genetic constructs are incorporated into host cells for amplification by first fusing the genetic constructs with a cloning vectors, such as phages or plasmids. Then the cloning vectors are inserted into hosts, preferably *E. coli*'s. Following the expressions of the recombinant genes in host cells, the resultant proteins can be isolated using conventional techniques.

Although recombinant techniques are provided for the production modified neurotoxins, recombinant techniques may also be employed to produce non-modified neurotoxins, for example botulinum toxin A as it exists naturally, since the genetic sequence of botulinum toxin type A is known.

There are many advantages to producing these neurotoxins recombinantly. For example, production of neurotoxin from anaerobic *Clostridium* cultures is a cumbersome and time-consuming process including a multi-step purification protocol involving several protein precipitation steps and either prolonged and repeated crystallization of the toxin or several stages of column chromatography. Significantly, the high toxicity of the product dictates that the procedure must be performed under strict containment (BL-3). During the fermentation process, the folded single-chain neurotoxins are activated by endogenous clostridial proteases through a process termed nicking. This involves the removal of approximately 10 amino acid residues from the single-chain to create the dichain form in which the two chains remain covalently linked through the intrachain disulfide bond.

The nicked neurotoxin is much more active than the unnicked form. The amount and precise location of nicking varies with the serotypes of the bacteria producing the toxin. The differences in single-chain neurotoxin activation and, hence, the yield of nicked toxin, are due to variations in the type and amounts of proteolytic activity produced by a given strain. For example, greater than 99% of *Clostridial botulinum* type A single-chain neurotoxin is activated by the Hall A *Clostridial botulinum* strain, whereas type B and E strains produce toxins with lower amounts of activation (0 to 75% depending upon the fermentation time). Thus, the high toxicity of the mature neurotoxin plays a major part in the commercial manufacture of neurotoxins as therapeutic agents.

The degree of activation of engineered clostridial toxins is, therefore, an important consideration for manufacture of these materials. It would be a major advantage if neurotoxins such as botulinum toxin and tetanus toxin could be expressed, recombinantly, in high yield in rapidly-growing bacteria (such as heterologous *E. coli* cells) as relatively non-toxic single-chains (or single chains having reduced toxic activity) which are safe, easy to isolate and simple to convert to the fully-active form.

With safety being a prime concern, previous work has concentrated on the expression in *E.coli* and purification of individual H and L chains of tetanus and botulinum toxins; these isolated chains are, by themselves, non-toxic; see Li et al., *Biochemistry* 33:7014-7020 (1994); Zhou et al., *Biochemistry* 34:15175-15181 (1995), hereby incorporated by reference herein. Following the separate production of these peptide chains and under strictly controlled conditions the H and L chains can be combined by oxidative disulphide linkage to form the neuroparalytic di-chains.

It is known that post operative pain resulting from (i.e. secondary to) a muscle spasm can be alleviated by pre-operative injection of botulinum toxin type A. *Developmental Medicine & Child Neurology* 42; 116-121:2000. Contrarily, our invention encompasses a method for treating postoperative pain by pre or peri-operative, peripheral administration of a botulinum toxin where the pain is not due to a spasmodic muscle.

Thus, a patient can either during surgery or up to about ten days prior to surgery (where the surgery is unrelated to correction of or treatment of a spasmodic muscle condition) be locally and peripherally administered by bolus injection with from about 20 units to about 300 units of a botulinum toxin, such a botulinum toxin type A, at or in the vicinity of the site of a prospective incision into the patient's dermis. The botulinum toxin injection can be subcutaneous or intramuscular. The surgery is not carried out to treat or to alleviate pain which results from a hyperactive or hypertonic muscle because we have surprisingly discovered that many types of pain which do not arise from or which do not result from a muscle spasm, can be significantly alleviated by practice of our disclosed invention.

According to our invention, for relief from post-operative pain, a patient who is scheduled for surgery for the purpose of tumor removal, bone graft, bone replacement, exploratory surgery, wound closure, a cosmetic surgery such as liposuction, or any of a myriad of other types of possible (non-muscle disorder treatment) surgical procedures which require one or more incisions into and/or through the patient's dermis can be treated, according to our invention, by peripheral administration of from about 0.01 U/kg to about 60 U/kg of a botulinum toxin, such as a botulinum toxin type A or B. The duration of significant post-operative pain alleviation can be from about 2 to about 6 months, or longer.

A method within the scope of the present invention can provide improved patient function. "Improved patient function" can be defined as an improvement measured by factors such as a reduced pain, reduced time spent in bed, increased ambulation, healthier attitude, more varied lifestyle and/or healing permitted by normal muscle tone. Improved patient function is synonymous with an improved quality of life (QOL). QOL can be assesses using, for example, the known SF-12 or SF-36 health survey scoring procedures. SF-36 assesses a patient's physical and mental health in the eight domains of physical functioning, role limitations due to physical problems, social functioning, bodily pain, general mental health, role limitations due to emotional problems, vitality, and general health perceptions. Scores obtained can be compared to published values available for various general and patient populations.

EXAMPLES

The following non-limiting examples provide those of ordinary skill in the art with specific preferred methods to treat non-spasm related pain within the scope of the present invention and are not intended to limit the scope of the invention. In the following examples various modes of non-systemic administration of a neurotoxin can be carried out. For example, by intramuscular bolus injection, by multiple subcutaneous injections at dermal sites at and in the region of pain or by implantation of a controlled release implant.

Example 1

Pain Alleviation by Peripheral Administration of Botulinum Toxin Type A

Two experiments were carried out. Sprague-Dawley rats (about 300 to about 350 grams) were used in both experiments. The neurotoxin used in both experiments was BOTOX® (botulinum toxin type A purified neurotoxin complex). In the first experiment there were 4 treatment (dose) groups: control (saline injected) rats (n=4), 7 U BOTOX®/kg rats (n=8), 15 U BOTOX® kg rats (n=5), and 30 U BOTOX®/kg rats (n=4). For the control rats, 25 microliters of 0.9% saline solution was injected subcutaneously into the plantar surface of the animal's hind paw. The site and route of administration of BOTOX® was the same as for the saline injection control group.

Five days after either the saline or BOTOX® injection, 50 microliters of 5% formalin was injected at the site on each of the rats in all four groups where either saline or BOTOX® had been previously injected. Limb lifting/licking by the subject animals was then recorded at 5 minute intervals for one hour.

The second set of experiment involved the same protocol as did the first experiment. In the second experiment there were three treatment (dose) groups: control (saline-injected) rats (n=3), 3.5 U/kg rats (n=7), and 7 U/kg rats (n=8); and the formalin test was conducted on the twelfth day after the original BOTOX® or saline injection.

The results of these two experiments are shown on FIGS. 1 and 2, respectively. The first 5 to 10 minutes can be referred to as phase 1, which is followed by phase 2. As shown by FIGS. 1 and 2, at both 5 days and 12 days after injection, there was a significant dose dependant pain alleviation in the BOTOX® treated animals.

Example 2

Peripheral Administration of a Botulinum Toxin to Alleviate a Non Spasm Pain

A 46 year old woman presents with pain localized at the deltoid region due to an arthritic condition. The muscle is not in spasm, nor does it exhibit a hypertonic condition. The patient is treated by a bolus injection of between about 50 Units and 200 units of intramuscular botulinum toxin type A. Within 1-7 days after neurotoxin administration the patient's pain is substantially alleviated. The duration of significant pain alleviation is from about 2 to about 6 months. A pain in the shoulder, arm, and hand due to osteoporosis, fixation of joints, coronary insufficiency, cervical osteoarthritis, localized shoulder disease, or due to a prolonged period of bed rest can be similarly treated.

Example 3

Peripheral Administration of a Neurotoxin to Treat Postherpetic Neuralgia

Postherpetic neuralgia is one of the most intractable of chronic pain problems. The patients suffering this excruciatingly painful process often are elderly, has debilitating disease, and are not suitable for major interventional procedures. The diagnosis is readily made by the appearance of the healed lesions of herpes and by the patient's history. The pain is intense and emotionally distressing. Postherpetic neuralgia may occur any where, but is most often in the thorax.

A 76 year old man presents a postherpetic type pain. The pain is localized to the abdomen region. The patient is treated by a bolus injection of between about 50 Units and 200 units of botulinum toxin type A subcutaneously to the abdominal region. Within 1-7 days after neurotoxin administration the patient's pain is substantially alleviated. The duration of significant pain alleviation is from about 2 to about 6 months.

Example 4

Peripheral Administration of a Neurotoxin to Treat Nasopharyngeal Tumor Pain

These tumors, most often squamous cell carcinomas, are usually in the fossa of Rosenmuller and may invade the base of the skull. Pain in the face is common. It is constant, dull-aching in nature.

A 35 year old man presents a nasopharyngeal tumor type pain. Pain is reported in the lower left cheek. The patient is treated by a bolus injection of between about 10 units and about 35 units of botulinum toxin type A intramuscularly to the cheek. Within 1-7 days after neurotoxin administration the patient's pain is substantially alleviated. The duration of significant pain alleviation is from about 2 to about 6 months.

Example 5

Peripheral Administration of a Neurotoxin to Treat Chronic Inflammatory Pain

A patient, age 45, presents with chronic inflammatory pain in the chest region. The patient is treated by a bolus injection of between about 50 Units and 200 units of intramuscular botulinum toxin type A. Within 1-7 days after neurotoxin administration the patient's pain is substantially alleviated. The duration of significant pain alleviation is from about 2 to about 6 months.

Example 6

Peripheral Administration of a Neurotoxin to Treat Pain Caused by Burns

A patient, age 51, experiencing pain subsequent to a severe and extensive first or second degree burns to the arm. The patient is treated by a bolus injection of between about 30 units to about 200 units of botulinum toxin type A, subcutaneously to the arm. Within 1-7 days after neurotoxin administration the patient's pain is substantially alleviated. The duration of significant pain alleviation is from about 2 to about 6 months.

Example 7

Peripheral Administration of a Neurotoxin to Treat Joint Pain

A patient, age 63, suffering from joint pain resulting from arthritis. The patient is treated by a bolus injection of between about 30 Units and 150 units of intramuscular botulinum toxin type A into the region of the painful joint. Within 1-7 days after neurotoxin administration the patient's pain is substantially alleviated. The duration of significant pain alleviation is from about 2 to about 6 months.

Example 8

Peripheral Administration of a Neurotoxin to Treat Post-Operative Pain

A patient, age 39, from 1 hour to ten days prior to surgery, is locally and peripherally administered by bolus injection or subcutaneous injection with from about 20 units to about 300 units of a botulinum toxin, such a botulinum toxin type A, at or in the vicinity of the site of a prospective incision into the patient's dermis. The botulinum toxin injection can be subcutaneous or intramuscular. The surgery is not carried out to treat or to alleviate a muscle disorder, such as a hyperactive or hypertonic muscle. The duration of significant post-operative pain alleviation is from about 2 to about 6 months.

Example 9

Treatment of Visceral Pain by Administration of a Neurotoxin

A male patient age 46 presents with chronic abdominal pain of visceral origin but of unknown etiology. Tumor or duct constriction is hypothesized. Subcutaneous or intraorgan botulinum toxin, such as from about 20 units to about 300 units of a botulinum toxin type A, is administered subcutaneously or intraorgan (at the site of the perceived pain). Within one to seven days the pain is substantially alleviated. The duration of significant pain alleviation is from about 2 to about 6 months.

Although the present invention has been described in detail with regard to certain preferred methods, other embodiments, versions, and modifications within the scope of the present invention are possible. For example, a wide variety of neurotoxins can be effectively used in the methods of the present invention. Additionally, the present invention includes peripheral administration methods to alleviate non-muscle disorder related pain wherein two or more neurotoxins, such as two or more botulinum toxins, are administered concurrently or consecutively. For example, botulinum toxin type A can be administered until a loss of clinical response or neutralizing antibodies develop, followed by administration of botulinum toxin type E. Alternately, a combination of any two or more of the botulinum serotypes A-G can be locally administered to control the onset and duration of the desired therapeutic result. Furthermore, non-neurotoxin compounds can be administered prior to, concurrently with or subsequent to administration of the neurotoxin to proved adjunct effect such as enhanced or a more rapid onset of denervation before the neurotoxin, such as a botulinum toxin, begins to exert its therapeutic effect.

We claim:

1. A method for alleviating neuropathic pain due to a disease, wherein the disease is diabetes, the method comprising the step of peripheral administration of an effective amount of a botulinum toxin to a human patient, thereby alleviating the neuropathic pain, wherein the pain treated is not due to a headache or a muscle spasm.

2. The method according to claim 1, wherein the botulinum toxin is selected from the group consisting of botulinum toxin types A, B, $C_1$, D, E, F and G.

3. The method of claim 1, wherein the pain alleviation is from about 2 to about 6 months.

4. The method of claim 1, wherein peripheral administration is selected from the group consisting of intramuscular, intraglandular, and subcutaneous administration routes.

5. A method for alleviating neuropathic pain due to diabetes, the method comprising the step of peripheral administration of an effective amount of botulinum toxin type A to a human patient, to thereby alleviate the neuropathic pain, wherein the pain treated is not due to a headache or a muscle spasm.

6. The method of claim 5, wherein peripheral administration is selected from the group consisting of intramuscular, intraglandular, and subcutaneous administration routes.

7. A method for alleviating neuropathic pain due to diabetes, the method comprising the step of peripheral administration of an effective amount of botulinum toxin type A to a human patient, thereby alleviating neuropathic pain due to diabetes, wherein the neuropathic pain treated is not due to a headache or a muscle spasm and neuropathic pain alleviation due to diabetes is from about 2 to about 6 months.

8. The method of claim 7, wherein peripheral administration includes intramuscular, intraglandular, and subcutaneous administration routes.

9. The method of claim 7, wherein the botulinum toxin is administered in an amount between about 0.01 U/kg and about 35 U/kg.

* * * * *

UNITED STATES PATENT AND TRADEMARK OFFICE
CERTIFICATE OF CORRECTION

PATENT NO. : 7,468,189 B2
APPLICATION NO. : 11/942985
DATED : December 23, 2008
INVENTOR(S) : Aoki et al.

It is certified that error appears in the above-identified patent and that said Letters Patent is hereby corrected as shown below:

On the Title page, in field (56), under "Other Publications", in column 2, line 17, delete "Wl J." and insert -- W. J. --, therefor.

Title page 2, in field (56), under "Other Publications", in column 1, line 14, delete "Efffects" and insert -- Effects --, therefor.

Title page 2, in field (56), under "Other Publications", in column 2, line 18, after "of" delete "a".

In column 5, line 57, delete "C," and insert -- $C_1$ --, therefor.

In column 7, line 8, delete "Furthermore." and insert -- Furthermore, --, therefor.

In column 11, line 50-51, after "acetylcholine" insert -- . --.

Signed and Sealed this

Seventeenth Day of March, 2009

JOHN DOLL
*Acting Director of the United States Patent and Trademark Office*